US012731525B2

(12) United States Patent
Maa et al.

(10) Patent No.: US 12,731,525 B2
(45) **Date of Patent: *Sep. 8, 2026**

(54) DIGITAL DISPLAY APPARATUS WITH DUAL REFRESH FREQUENCIES

(71) Applicant: Aleddra Inc., Renton, WA (US)

(72) Inventors: Chia-Yiu Maa, Bellevue, WA (US); Li-Jyuan Luo, Taipei City (TW)

(73) Assignee: Aleddra Inc., Renton, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/253,662

(22) Filed: Jun. 27, 2025

(65) Prior Publication Data

US 2026/0038418 A1 Feb. 5, 2026

Related U.S. Application Data

(63) Continuation-in-part of application No. 19/227,439, filed on Jun. 3, 2025, and a continuation-in-part of (Continued)

(51) Int. Cl.
*G09G 3/20* (2006.01)
*A61M 21/00* (2006.01)

(52) U.S. Cl.
CPC .......... *G09G 3/2096* (2013.01); *A61M 21/00* (2013.01); *A61M 2021/005* (2013.01);

(Continued)

(58) Field of Classification Search
None
See application file for complete search history.

(56) References Cited

U.S. PATENT DOCUMENTS

2014/0058483 A1* 2/2014 Zao .......................... A61N 5/06 607/88
2016/0291920 A1* 10/2016 Sirpal ..................... G06F 16/54

(Continued)

FOREIGN PATENT DOCUMENTS

WO WO-2023107024 A1 * 6/2023 ........... A61N 5/0618

OTHER PUBLICATIONS

Binaural Gamma Sinus 80 Hz—L 120 Hz—R, 2019, Brainstate, https://open.spotify.com/track/1NtOid2GxikfUkQajrvWye (Year: 2019).*

(Continued)

*Primary Examiner* — Kirk W Hermann
(74) *Attorney, Agent, or Firm* — Andy M. Han; Han IP PLLC

(57) ABSTRACT

A digital display apparatus comprises a controller and a digital pixel panel. The pixels of the digital pixel panel are divided into a first group of pixels and a second group of pixels. The controller is configured to operate the first group of pixels at a first flicker-free refresh frequency F1 and to operate the second group of pixels at a second flicker-free refresh frequency F2>F1. When the graphic content displayed on the digital pixel panel is viewed by a subject, an invisible visual stimulation at a harmonic frequency (HF) equal to |2F1−F2| is induced endogenously in a brain of the subject. By properly choosing F1 and F2, and subsequently HF, the digital display apparatus offers the benefits of preventing or improving Alzheimer's disease or memory recall.

11 Claims, 2 Drawing Sheets

Related U.S. Application Data application No. 19/065,863, filed on Feb. 27, 2025, which is a continuation-in-part of application No. 18/791,703, filed on Aug. 1, 2024, now Pat. No. 12,374,263.

(52) U.S. Cl.
CPC ............... *G09G 2300/0804* (2013.01); *G09G 2320/0247* (2013.01); *G09G 2320/0673* (2013.01); *G09G 2320/106* (2013.01); *G09G 2340/0435* (2013.01)

(56) References Cited

U.S. PATENT DOCUMENTS

2023/0104621 A1* 4/2023 Malchano ............. A61B 5/378
600/544
2023/0256262 A1* 8/2023 Carstensen ........... A61B 5/375
607/88

OTHER PUBLICATIONS

Jerry Grillo, Finding flicker's therapeutic pathway, opening the door to non-invasive treatments for neurodegenerative diseases, Aug. 31, 2023, Medical press, https://medicalxpress.com/news/2023-08-flicker-therapeutic-pathway-door-non-invasive.html, pp. 1-4 (Year: 2023).*

* cited by examiner

DIGITAL DISPLAY APPARATUS WITH DUAL REFRESH FREQUENCIES

The present disclosure is a continuation-in-part (CIP) of U.S. patent application Ser. No. 19/065,863, filed 27 Feb. 2025, which itself is a CIP of U.S. patent application Ser. No. 18/791,703, filed 1 Aug. 2024. The present disclosure is also a CIP of U.S. patent application Ser. No. 19/227,439, filed 3 Jun. 2025. Contents of aforementioned applications are herein incorporated by reference in their entirety.

BACKGROUND

Technical Field

The present disclosure pertains to the field of digital display apparatus and, more specifically, proposes digital display apparatus with dual refresh frequencies.

Description of Related Art

In U.S. patent application Ser. No. 18/791,703, filed 1 Aug. 2024, it introduced a display device comprising a controller and a two-dimensional digital pixel panel. A plurality of pixels of the two-dimensional digital pixel panel are divided into a first group of pixels and a second group of pixels. The controller is configured to display a graphic content via the two-dimensional digital pixel panel. The controller is configured to operate the first group of pixels at a first flicker-free refresh frequency (F1)≥60 Hz. The controller is configured to operate the second group of pixels at a second flicker-free refresh frequency (F2)≥60 Hz, different than F1. An invisible visual simulation to a subject viewing the digital display device is induced at a frequency equal to a difference between F1 and F2. In U.S. patent application Ser. No. 19/065,863, which is a CIP U.S. patent application Ser. No. 18/791,703, the digital display device is expanded to a display system comprising a first digital display and a second digital display, where the first digital display is configured to operate at F1 and the second digital display is configured to operate at F2.

In U.S. patent application Ser. No. 19/227,439, it introduced a digital display apparatus comprises a controller, a first light source, and a second light source. The controller is configured to operate the first light source at a first frequency F1≥60 Hz generating a first light output. Moreover, the controller is configured to operate the second light source at a second frequency F2 (>F1) generating a second light output. When the first light output and the second light output are perceived by a subject simultaneously, an invisible visual simulation at a harmonic frequency (HF) equal to |2F1−F2| is induced endogenously in a brain of the subject. By carefully choosing F1 and F2, and subsequently HF, the digital display apparatus may be used for treating or preventing Alzheimer's disease.

The present disclosure applies the invention introduced in U.S. patent application Ser. No. 19/227,439 to the digital display device introduced in U.S. patent application Ser. No. 18/791,703 and the dual-display system introduced in Ser. No. 19/065,863, thus generalizing the selection of F1 and F2 for the digital display device introduced in U.S. patent application Ser. No. 18/791,703 and the dual-display system introduced in Ser. No. 19/065,863. By properly choosing F1 and F2, and subsequently HF, the digital display apparatus offers the benefits of preventing or improving Alzheimer's disease or memory recall.

SUMMARY

In one aspect, the digital display apparatus comprises a controller and a digital pixel panel. The pixels of the digital pixel panel are divided into a first group of pixels and a second group of pixels. The controller is configured to display a graphic content via the digital pixel panel. The controller is configured to operate the first group of pixels at a first flicker-free refresh frequency (F1)≥60 Hz. The controller is configured to operate the second group of pixels at a second flicker-free refresh frequency (F2)>F1. When the graphic content displayed on the digital pixel panel is viewed by a subject, an invisible visual simulation at a harmonic frequency (HF) equal to |2F1−F2| is induced endogenously in a brain of the subject. F1 is flicker-free for F1≥60 Hz, and F2 is flicker-free for F2>F1≥60 Hz. Moreover, HF is invisible because it is induced endogenously in the brain of the subject. The digital display apparatus does not emit such HF directly. |2F1−F2| refers to the absolute value of the difference of 2F1 and F2. In other words, their difference at 40 Hz and −40 Hz are the same as far as inducing an endogenously stimulation in the brain of the subject is concerned, In some embodiments, HF is between 20 Hz and 45 Hz. In practice, HF may be more narrowly chosen to be between 35 Hz and 40 Hz, thus generating gamma stimulation in the brain of the subject for treating or preventing Alzheimer's disease.

In some embodiments, F1 is 80 Hz and F2 is 120 Hz, and thus HF=|2F1−F2|=40 Hz. Similarly, F1 is 80 Hz and F2 is 200 Hz would also generate HF=|2F1−F2|=40 Hz.

In some embodiments, F1 is 65 Hz and F2 is 90 Hz.

In some embodiments, F1 is 70 Hz and F2 is 100 Hz.

In some embodiments, F1 is 75 Hz and F2 is 110 Hz.

In some embodiments, F1 is 85 Hz and F2 is 130 Hz.

In some embodiments, F1 is 90 Hz and F2 is 140 Hz.

Other research has shown that the slow theta stimulation at 4 Hz and 7 Hz has the effect of triggering memory recall. The present disclosure can be easily devised to support slow theta stimulation. In some embodiments, HF is between 3 Hz and 10 Hz.

In some embodiments, F1 is 60 Hz and F2 is 116 Hz, resulting in HF=4 Hz. In some other embodiments, F1 is 60 Hz and F2 is 124 Hz, also resulting in HF=4 Hz.

In some embodiments, the first group of pixels occupies the top section of the digital pixel panel and the second group of pixels occupies the bottom section of the digital pixel panel as shown in FIG. 2. The white dots in FIG. 2 denote the pixels in the first group of pixels and the black dots denote the pixels in the second group of pixels. Other layout arrangements for the first group of pixels and the second group pixels are possible. However, separating the first group of pixels and the second group of pixels in disjoint regions simplifies the hardware design of the controller and minimizes the perceptibility of refresh frequency discrepancy between the first group of pixels and the second group pixels.

In some embodiments, the controller having two display channels. The first display channel feeds graphic content to the first group of pixels and the second display channel feeds graphic content to the second group of pixels.

In some embodiments, the digital pixel panel comprises a first physical digital pixel panel and a second physical display panel. In which case, the controller is configured to operate the first physical digital pixel panel at F1 refresh frequency and the second physical display pixel panel at F2 refresh frequency. Examples include but are not limited to dual-monitor computer systems, dual-screen smartphones, and dual-lens digital goggles. With a dual-monitor computer system of the present disclosure, one monitor operates at F1 refresh frequency and the other monitor at F2 refresh frequency. The controller in this case may include the graphic controller of the host computer, the hardware responsible for refreshing the first monitors at F1, and the hardware responsible for refreshing the second monitor at F2. The controller determines which content will be displayed in the first monitor and which content will be displayed at the other monitor. Similarly, for a dual-screen smartphone of the present disclosure, one screen operates at F1 and the other screen at F2. For a dual-lens digital google of the present disclosure, one digital lens operates at F1 and the other digital lens at F2.

BRIEF DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of digital display apparatuses having different form factors.

A digital display apparatus comprises a controller and a digital pixel panel. The pixels of the digital pixel panel are divided into a first group of pixels and a second group of pixels. The controller is configured to operate the first group of pixels at a first flicker-free refresh frequency F1 and to operate the second group of pixels at a second flicker-free refresh frequency F2>F1. When the graphic content displayed on the digital pixel panel is viewed by a subject, an invisible visual simulation at a harmonic frequency (HF) equal to $|2F1-F2|$ is induced endogenously in a brain of the subject.

EXAMPLE IMPLEMENTATIONS

Figure 1:
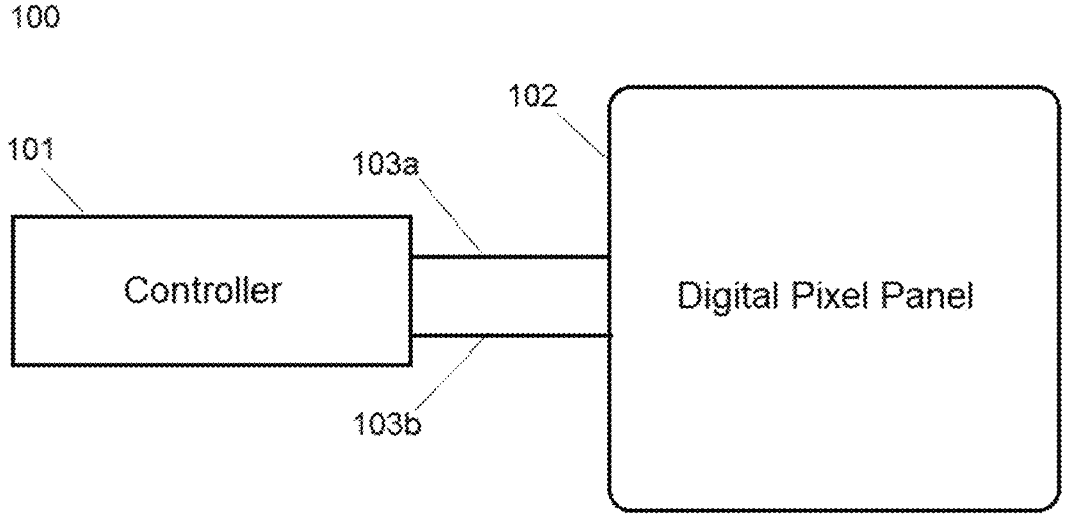
FIG. 1 schematically depicts an embodiment of the present disclosure.
Figure 2:
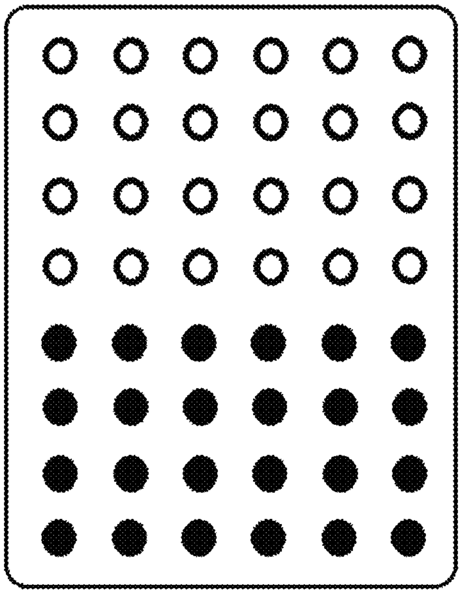
FIG. 2 schematically depicts an embodiment of the present disclosure having the first group of pixels on the top section of the digital pixel panel and the second group of pixels on the bottom section of the digital pixel panel.

FIG. 1 shows an embodiment of the digital display apparatus of the present disclosure 100. It comprises a controller 101 and a digital pixel panel 102. The pixels of the digital pixel panel 102 are divided into a first group of pixels and a second group of pixels as shown in FIG. 2. The white dots in FIG. 2 denote the pixels in the first group of pixels and the black dots denote the pixels in the second group of pixels. Controller 101 has two channels 103*a*,103*b*. Controller 101 feeds graphic content through channel 103*a* to the first group of pixels at 80 Hz. Similarly, controller 101 feeds graphic content through the second display channel 103*b* to the second group of pixels at 120 Hz. When a subject views the digital pixel panel 102, the subject is exposed to both F1 (80 Hz) and F2 (120 Hz) refresh frequencies, thus an HF at 40 Hz is induced endogenously in a brain of the subject. The embodiment 100 is thus suitable for treating or preventing Alzheimer's disease. Other combinations may be chosen for F1 and F2, such as (65 Hz, 90 Hz), (70 Hz, 100 Hz), (75 Hz, 110 Hz), (85 Hz, 130 Hz), (90 Hz, 140 Hz), etc.

The embodiment 100 can be revised to support slow theta stimulation by selecting F1=60 Hz and F2=116 Hz (or F2=124 Hz), resulting in HF=4 Hz. These embodiments are suitable for treating or preventing memory loss.

Figure 3:
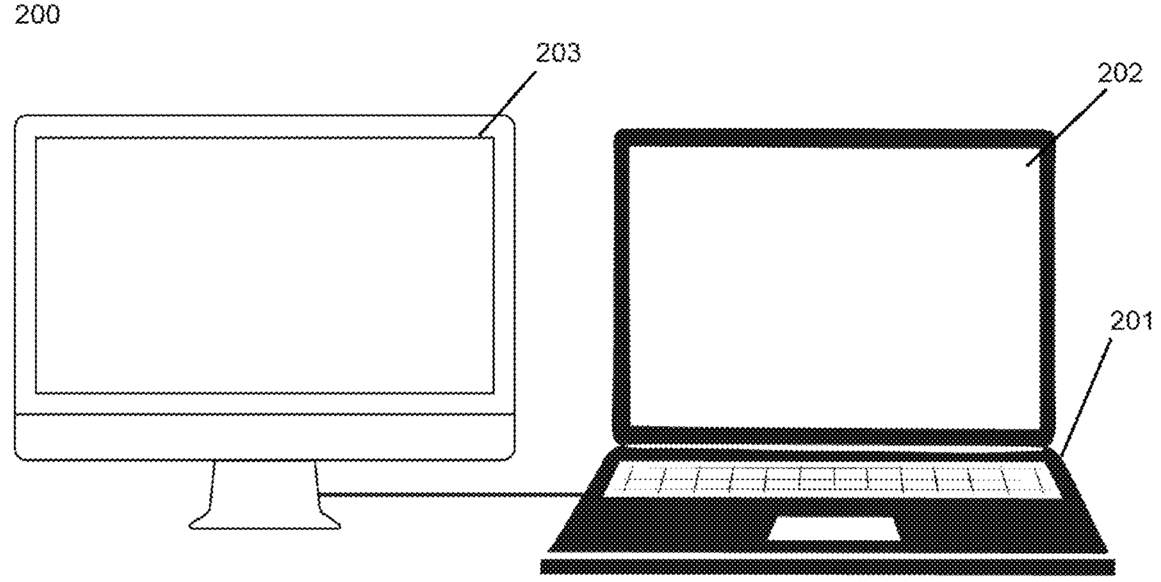
FIG. 3 schematically depicts an embodiment of the present disclosure as a computer system with dual monitors.

FIG. 3 shows an embodiment of the present disclosure 200 as a computer system with dual monitors. The laptop computer 201 has an integrated monitor 202 operating at 80 Hz refresh frequency. The extended monitor 203 has a 120 Hz refresh frequency. The (host) laptop computer controls and manages contents of both its integrated monitor 202 (the first physical digital pixel panel) and the extended monitor 203 (the second physical pixel panel). The content displayed in the integrated monitor 202 is not required to be correlated to the content displayed in the extended monitor 203. For example, the integrated monitor may show a Word document whereas the extended monitor may show a video. When a subject views the integrated monitor 202 and the extended monitor 203 simultaneously, the subject is exposed to both F1 (80 Hz) and F2 (120 Hz) refresh frequencies, thus an HF at 40 Hz is induced endogenously in a brain of the subject. The embodiment 200 is thus suitable for treating or preventing Alzheimer's disease. Other combinations may be chosen for F1 and F2, such as (65 Hz, 90 Hz), (70 Hz, 100 Hz), (75 Hz, 110 Hz), (85 Hz, 130 Hz), (90 Hz, 140 Hz), etc.

The embodiment 200 can be revised to support slow theta stimulation by selecting F1=60 Hz and F2=116 Hz (or F2=124 Hz), resulting in HF=4 Hz. These embodiments are suitable for treating or preventing memory loss.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A digital display apparatus comprising:

a controller; and a digital pixel panel, wherein:

- a plurality of pixels of the digital pixel panel are divided into a first group of pixels and a second group of pixels,
- the controller is configured to display a graphic content via the digital pixel panel,
- the controller is configured to operate the first group of pixels at a first flicker-free refresh frequency $(F1) \geq 60$ Hz,
- the controller is configured to operate the second group of pixels at a second flicker-free refresh frequency $(F2) > F1$, and
- when the graphic content displayed on the digital pixel panel is viewed by a subject, an invisible visual stimulation at a harmonic frequency (HF) equal to $|2F1-F2|$ is induced endogenously in a brain of the subject, wherein, HF is either:
- between 20 Hz and 45 Hz, or
- between 3 Hz and 10 Hz; and wherein the digital display apparatus operates at one of a plurality of combinations of F1 and F2 other than a combination of F1 and F2 in which F1=80 Hz and F2=120 Hz.

2. The apparatus of claim 1, wherein F1 is 65 Hz and F2 is 90 Hz.

3. The apparatus of claim 1, wherein F1 is 70 Hz and F2 is 100 Hz.

4. The apparatus of claim 1, wherein F1 is 75 Hz and F2 is 110 Hz.

5. The apparatus of claim 1, wherein F1 is 85 Hz and F2 is 130 Hz.

6. The apparatus of claim 1, wherein F1 is 90 Hz and F2 is 140 Hz.

7. The apparatus of claim 1, wherein F1 is 60 Hz and F2 is 116 Hz.

8. The apparatus of claim 1, wherein F1 is 60 Hz and F2 is 124 Hz.

9. The apparatus of claim 1, wherein the first group of pixels occupies a top section of the digital pixel panel and the second group of pixels occupies a bottom section of the digital pixel panel.

10. The apparatus of claim 1, wherein the controller is configured with two display channels comprising a first display channel and a second display channel, wherein the first display channel feeds the graphic content to the first group of pixels and the second display channel feeds the graphic content to the second group of pixels.

11. The apparatus of claim 1, wherein the digital pixel panel comprises a first physical digital pixel panel and a second physical display panel, and wherein the controller is configured to operate the first physical digital pixel panel at F1 refresh frequency and the second physical display pixel panel at F2 refresh frequency.

* * * * *